United States Patent
Murthy et al.

(10) Patent No.: US 6,596,866 B2
(45) Date of Patent: Jul. 22, 2003

(54) PROCESS FOR THE PREPARATION OF NEFAZODONE HYDROCHLORIDE

(75) Inventors: K. S. Keshava Murthy, Brantford (CA); Bhaskar Reddy Guntoori, Brantford (CA); Daqing Che, Brantford (CA)

(73) Assignee: Brantford Chemicals Inc., Brantford (CA)

( * ) Notice: Subject to any disclaimer, the term of this patent is extended or adjusted under 35 U.S.C. 154(b) by 12 days.

(21) Appl. No.: 09/953,167

(22) Filed: Sep. 17, 2001

(65) Prior Publication Data

US 2003/0078423 A1 Apr. 24, 2003

(30) Foreign Application Priority Data

Sep. 10, 2001  (CA) ............................................. 2356450

(51) Int. Cl.[7] ............................................. C07D 403/06

(52) U.S. Cl. ...................... 544/366; 544/393

(58) Field of Search ......................................... 544/366

(56) References Cited

U.S. PATENT DOCUMENTS

| 4,338,317 A | | 7/1982 | Temple, Jr. et al. ......... 424/250 |
| 5,256,664 A | * | 10/1993 | Mayol et al. |
| 5,900,485 A | | 5/1999 | Lei et al. .................... 544/366 |

FOREIGN PATENT DOCUMENTS

| CA | 1198436 | 12/1985 |
| CA | 1233826 | 3/1988 |
| EP | 1 000 944 | 5/2000 |

* cited by examiner

*Primary Examiner*—Emily Bernhardt
(74) *Attorney, Agent, or Firm*—Marcelo K. Sarkis; Kitt Sinden; Ivor M. Hughes

(57) ABSTRACT

A process for the preparation of Nefazodone hydrochloride comprising direct conversion of semicarbazide dihydrochloride 3 into Nefazodone hydrochloride which process involves a reaction of triethyl orthopropionate in the presence of trimethylsilylchloride and hydrochloric acid.

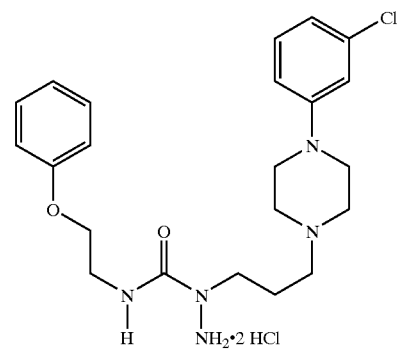

Semicarbazide Dihydrochloride 3

14 Claims, No Drawings

PROCESS FOR THE PREPARATION OF NEFAZODONE HYDROCHLORIDE

FIELD OF THE INVENTION

This invention relates to processes for the preparation of Nefazodone Hydrochloride.

BACKGROUND OF THE INVENTION

Nefazodone[2-[3-[4-(3-Chlorophenyl)-1-piperazinyl] propyl]-5-ethyl-2,4-dihydro-4-(2-phenoxyethyl)-3H-1,2,4-triazol-3-one; 2-[3-[4-(3-chlorophenyl)-1-piperazinyl]-propyl]-5-ethyl-4-(2-phenoxyethyl)-2H-1,2,4-triazol-3 (4H)-one] bears the following structural formula:

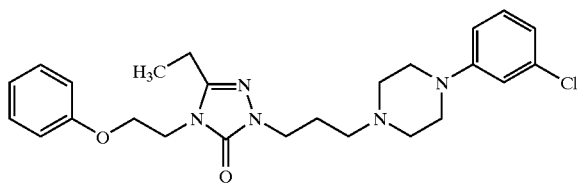

One of the forms of Nefazodone marketed is the hydrochloride form.

Canadian Letter Patent 1,198,436 and its corresponding U.S. Pat. No. 4,338,317 disclose a process for the manufacture of Nefazodone free base and Nefazodone hydrochloride. The above patents purport to claim a process involving the reaction of 2-piperazinylalkyltriazolone with suitable phenoxyalkylhalide to form Nefazodone free base. The Nefazodone free base is then converted to Nefazodone hydrochloride by using hydrogen chloride.

Canadian Patent 1,233,826 disclosed a purported improved process in which the Nefazodone free base is produced by reacting a phenoxyalkylcarbamate with an N-substituted hydrazide of a carboxylic acid.

U.S. Pat. No. 5,900,485 describes another process for preparing Nefazodone from semicarbazide dihydrochloride 3 and triethyl orthopropionate in the presence of hydrochloride.

Processes described in the Canadian Letter Patent 1,198, 436, U.S. Pat. No. 4,338,317 and Canadian Patent 1,233,826 for the preparation of Nefazodone hydrochloride involve the preparation of Nefazodone free base first and then the conversion of it to Nefazodone hydrochloride.

The process of reacting an amine base with hydrogen chloride is a standard textbook reaction in most cases. The reaction of substituted piperazines with hydrogen chloride is not as simple as it seems however. There are two problems.

The first problem is that the product of this reaction often crystallizes in the form of a solvate or hydrate, i.e. the solid hydrochloride salt contains water (or some other solvent). An example of this is seen at page 20, lines 14–18 of Canadian Letters Patent 1,198,436. The hydrate of a hydrochloride salt does not have the same chemical and physical properties as the solvent free form. Further the process of reacting nefazodone with hydrogen chloride does not always produce a single form such as the anhydrous monohydrochloride salt of nefazodone.

The second problem is that nefazodone is an arylpiperazine, which means that it has a second basic site. Reacting the free base of an arylpiperazine with hydrogen chloride must be carried out under strict control of conditions if the monohydrochloride salt is to be the only result. Example 2(a) at page 20, lines 12–17 of Canadian Letters Patent 1,198,436 teaches the preparation of the HCl salt of nefazodone (as a hydrate) by "acidifying a solution of the free base in ethanol with ethanolic hydrogen chloride, and crystallization to afford hydrate . . . ". Clearly, therefore the formation of an HCl salt is not without complications which must be allowed for to arrive at the final desired product.

The experimental evidence in example 2 of the Patent shows the analysis for a mono-hydrochloride but does not specify the means by which it was made or the amount of HCl used. Was it formed cleanly, or was the final pure salt only reached by extensive purification of a mixture of HCl salts? In fact the starting free base is noted as having been formed in 94% yield, but when the mono-hydrochloride is formed the yield is given as only 30.7%. This large loss requires the need to separate out other formed salts and teaches that the claimed mono-hydrochloride is not the only product formed on adding HCl in ethanol to the free base.

The HCl salt finally isolated is itself a hydrate, implying also the difficulty attending to the formation of solvates of the salt in the process. The production of the hydrate would depend on the conditions used in the reactions including the solvent. At the end of example 2 is a notation that a non-hydrated sample can be formed "according to the above process". The "above process" was said to give a hydrate, and so something else undisclosed must have been done to yield "a sample" fortuitously non-hydrated, and the yield here is also not stated. Finally, it is suspicious that all the spectral detail to characterize the hydrochloride was taken on the hydrated sample even though only the non-hydrated form was claimed.

Similar descriptions of procedures for preparing HCl salts appear at page 21, lines 21–23; page 22, lines 20–22; page 23, lines 17–19; and page 29, lines 18–21.

Thus the reaction of nefazodone and hydrogen chloride is not a simple reaction and depending upon the conditions, solvents (vehicle in which the reaction proceeds), order of addition of reactants to the solvent and amounts of reactants, these criteria will determine the form of Nefazodone produced.

U.S. Pat. No. 5,900,485 describes a process which deals with a direct one-pot conversion of semicarbazide dihydrochloride 3 to Nefazodone hydrochloride. This process suffers from lower yield with 45%. The purity of the product obtained was only 95% and required further purification to obtain pharmaceutically acceptable samples.

It is therefore an object of the invention to provide an improved and higher yielding process for the manufacture of Nefazodone hydrochloride.

It is a further object of the invention to provide a process for the manufacture of Nefazodone hydrochloride directly from the semicarbazide dihydrochloride.

Further and other objects of the invention will become apparent to those skilled in the art when considering the following summary of the invention and the more detailed description of the preferred embodiments and examples described herein.

SUMMARY OF THE INVENTION

The present invention provides a novel and higher yielding and cost-effective process for the manufacture of Nefazodone hydrochloride. Unexpectedly, it has been found that the yield can be dramatically enhanced through the use of an additive or catalyst, for example trimethylsilyl chloride, which promotes the formation of the iminoester intermediate. The iminoester hydrochloride is then converted directly to Nefazodone hydrochloride in situ through cyclization in the presence of hydrochloride and an organic solvent.

Therefore according to one aspect of the invention there is provided a process comprising reacting semicarbazide dihydrochloride (i.e. Formula 3 below) with triethylorthopropionate using, for example, trimethysilylchloride and hydrochloric acid in alcohol to convert the semicarbazide dihydrochloride directly into Nefazodone Hydrochloride (i.e. Formula 4 below). Purification of the resulting Nefazodone Hydrochloride affords pure Nefazodone Hydrochloride.

According to yet another aspect of the invention there is provided a process for the preparation of Nefazodone Hydrochloride comprising reacting semicarbazide dihydrochloride with triethylorthopropionate using trimethylsilylchloride and hydrochloric acid to convert the semicarbazide dihydrochloride (i.e. Formula 3 below) into Nefazodone Hydrochloride (i.e. Formula 4 below) directly. Purification of crude Nefazodone Hydrochloride affords pure Nefazodone Hydrochloride.

According to yet another aspect of the invention there is provided a process for the preparation of Nefazodone Hydrochloride comprising:

(i) adding Semicarbazide (i.e. Formula 2 below) (445 g, 1.03 mol) in methanol (2000 mL) to hydrochloric acid (342 g, 2.58 eq) in isopropanol (27.5% w/w solution);

(ii) heating the mixture to reflux for 2.5 to 3.0 hours and subsequently cooling it to room temperature;

(iii) filtering the reaction mixture and washing the solid with methanol (500 mL) and subsequently drying same under vacuum to afford 429 g (85% molar) of Semicarbazide Dihydrochloride (i.e. Formula 3 below);

(iv) adding trimethylsilyl chloride (23.9 g, 0.22 mol) slowly to a suspension of Semicarbazide Dihydrochloride (i.e. Formula 3 below) (101 g, 0.20 mol) in ethanol (400 mL), followed by triethyl orthopropionate (141 g, 0.80 mol) and stirring for 14–16 hours;

(v) adding hydrochloric acid (26.6 g, 0.20 mol) in isopropanol (27.5% w/w) to the reaction mixture and stirring for 6–8 hours;

(vi) adding trimethylsilyl chloride (12.0 g, 0.11 mol) to the reaction mixture, followed by triethyl orthopropionate (35.3 g, 0.2 mol) and stirring for 12–14 hours;

(vii) adding hydrochloric acid (13.3 g, 0.10 mol) in isopropanol (27.5% w/w) to the reaction mixture and stirring for 2–3 hours;

(viii) adding heptane (400 mL) to the reaction mixture and stirring for 2–3 hours and subsequently distilling 400 mL of solvent mixture under reduced pressure and adding heptane (400 mL) and stirring for 4–6 hours;

(ix) filtering the reaction mixture as a damp product and washing same with 150 mL heptane and ethanol mixture (4:1) to afford crude Nefazodone Hydrochloride (i.e. Formula 4 below) (137 g, LOD 37.2%, 85% molar yield on dry basis);

(x) and preferably, for further processing, providing an overall molar yield from the intermediate Semicarbazide Dihydrochloride (i.e. Formula 3 below) in the order of 79%. In one embodiment part of the damp product (35.0 g) was recrystallized from isopropanol (520 mL) and acetone (25 mL) to afford 20.7 gm, 93% molar yield.

According to yet another aspect of the invention there is provided a process for the preparation of Nefazodone Hydrochloride comprising:

(i) preferably adding a predetermined amount of semicarbazide in methanol to a predetermined amount of hydrochloric acid in isopropanol;

(ii) preferably heating the mixture to reflux for a predetermined time period and subsequently cooling it to substantially room temperature;

(iii) preferably filtering the reaction mixture and washing the solid with methanol and subsequently drying same under vacuum to afford Semicarbazide Dihydrochloride;

(iv) adding a predetermined amount of trimethylsilyl chloride slowly to a suspension of Semicarbazide Dihydrochloride in ethanol, followed by a predetermined amount of triethyl orthopropionate and stirring for a predetermined period of time;

(v) adding a predetermined amount of hydrochloric acid in isopropanol to the reaction mixture and stirring for a predetermined amount of time;

(vi) adding a predetermined amount of trimethylsilyl chloride to the reaction mixture, followed by a predetermined amount of triethyl orthopropionate and stirring for a predetermined amount of time;

(vii) adding a predetermined amount of hydrochloric acid in isopropanol to the reaction mixture and stirring for a predetermined amount of time;

(viii) adding a predetermined amount of heptane to the reaction mixture and stirring for a predetermined amount of time and subsequently distilling a predetermined amount of solvent mixture under reduced pressure and adding heptane and stirring for 4a predetermined amount of;

(ix) filtering the reaction mixture as a damp product and washing same with heptane and ethanol mixture (4:1) to afford crude Nefazodone Hydrochloride;

(x) and preferably, for further processing, providing an overall molar yield from the intermediate Semicarbazide Dihydrochloride of 79%. In one embodiment part of the damp product was recrystallized from isopropanol and acetone.

According to yet another aspect of the invention there is provided a process for the manufacture of Nefazadone Hydrochloride comprising the following steps:

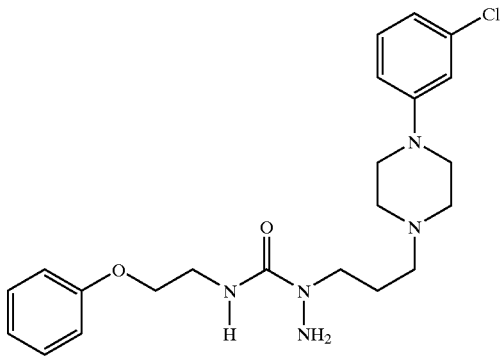

Semicarbazide 2
STEP 1

Hydrochloric acid in Alcohol | Methanol,

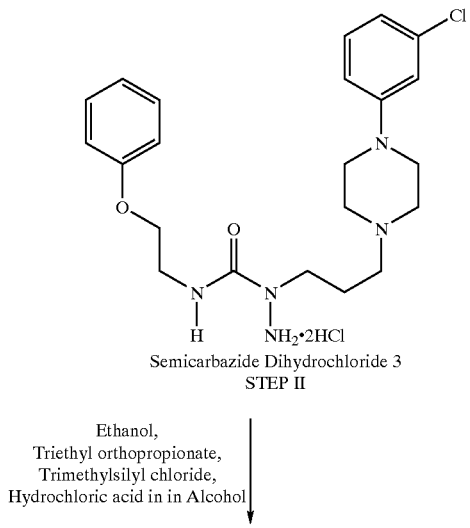

Semicarbazide Dihydrochloride 3
STEP II

Ethanol,
Triethyl orthopropionate,
Trimethylsilyl chloride,
Hydrochloric acid in in Alcohol

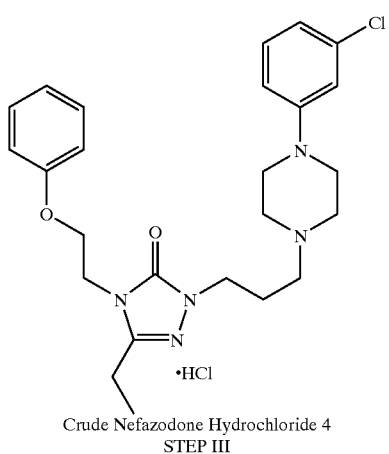

Crude Nefazodone Hydrochloride 4
STEP III and

Purification | Alcohol
or
Alcohol and Acetone
or
Alcohol and Water

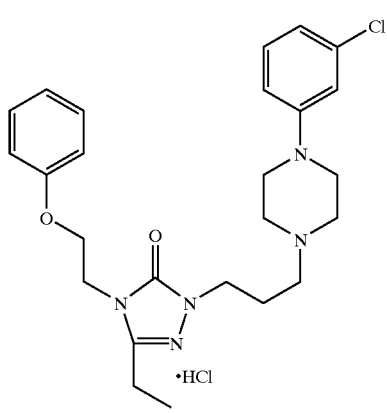

Pure Nefazodone Hydrochloride 1
STEP IV

According to yet another aspect of the invention there is provided a process for the preparation of Nefazodone Hydrochloride comprising the following steps:

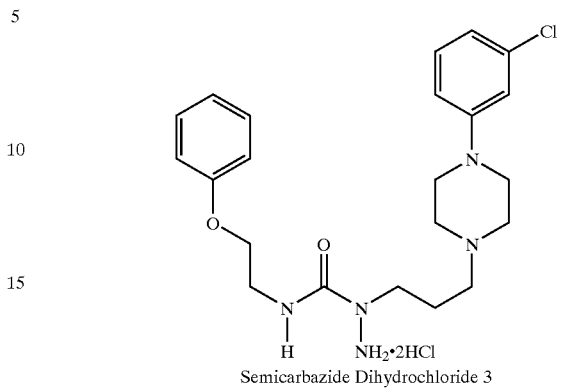

Semicarbazide Dihydrochloride 3
STEP I

Ethanol,
Triethyl orthopropionate,
Trimethylsilyl chloride,
Hydrochloric acid in Alcohol

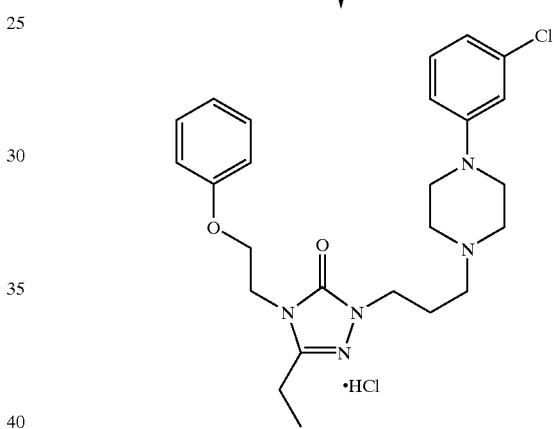

Crude Nefazodone Hydrochloride 4
STEP II

Preferably the Semicarbazide Dihydrochloride is prepared by the following steps:

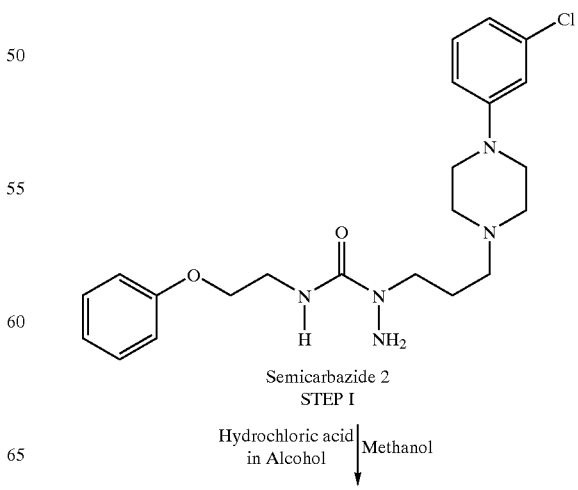

Semicarbazide 2
STEP I

Hydrochloric acid in Alcohol | Methanol

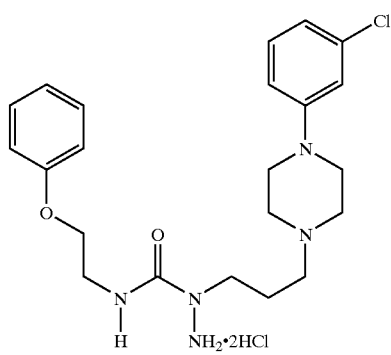

Semicarbazide Dihydrochloride 3
STEP II

Preferably the crude Nefazodone Hydrochloride of the above process may further be treated by the following steps:

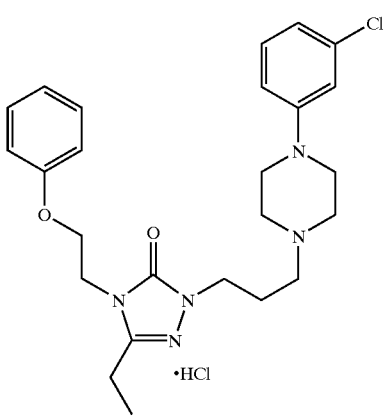

Crude Nefazodone Hydrochloride 4
Not isolated

Purification | Alcohol and Acetone or Alcohol and Water

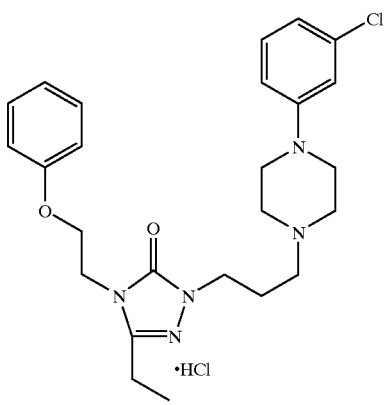

Pure Nefazodone Hydrochloride 1

According to yet another aspect of the invention there is provided a process for the preparation of Semicarbazide Dihydrochloride comprising the steps as follows:

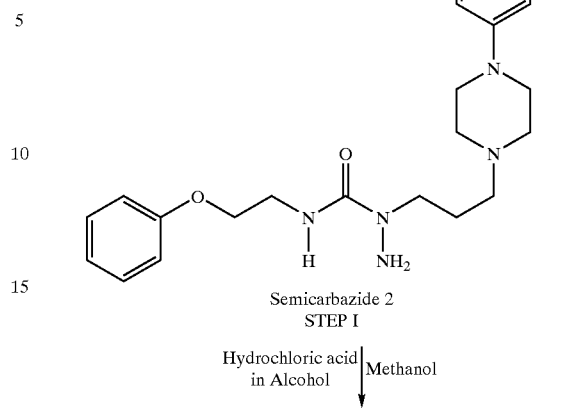

Semicarbazide 2
STEP I

Hydrochloric acid in Alcohol | Methanol

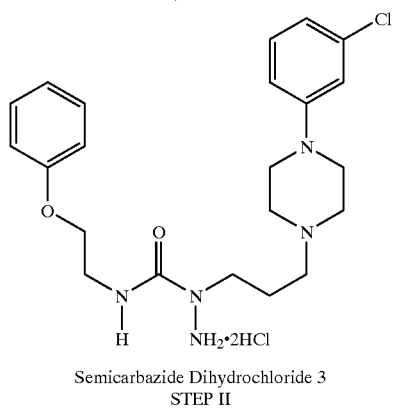

Semicarbazide Dihydrochloride 3
STEP II

The invention will now be illustrated with reference to the following examples which are to be interpreted as illustrative of the invention and not in a limiting sense.

Preparation of Semicarbazide Dihydrochloride (i.e. Formula 3 Above)

To a solution of Semicarbazide (i.e. Formula 2 above) (445 g, 1.03 mol) in methanol (2000 mL) was added hydrochloric acid (342 g, 2.58 eq) in isopropanol (27.5% w/w solution). The mixture is heated to reflux for 2.5 to 3.0 hours and was cooled to room temperature. The reaction mixture is filtered and the solid was washed with methanol (500 mL) and dried under vacuum to afford 429 g (85% molar) of Semicarbazide Dihydrochloride (i.e. Formula 3 above).

Procedure for Preparation of Crude Nefazodone Hydrochloride (i.e. Formula 4 Aabove) and Pure Nefazodone Hydrochloride (i.e. Formula 1 Above)

To a suspension of Semicarbazide Dihydrochloride (i.e. Formula 3 Above) (101 g, 0.20 mol) in ethanol (400 mL) was added trimethylsilyl chloride (23.9 g, 0.22 mol) slowly, followed by triethyl orthopropionate (141 g, 0.80 mol) and stirred for 14–16 hours. To the reaction mixture was added hydrochloric acid (26.6 g, 0.20 mol) in isopropanol (27.5% w/w) and stirred for 6-8 hours. To the reaction mixture was added trimethylsilyl chloride (12.0 g, 0.11 mol), followed by triethyl orthopropionate (35.3 g, 0.2 mol) and stirred for 12–14 hours. To the reaction mixture was added hydrochloric acid (13.3 g, 0.10 mol) in isopropanol (27.5% w/w) and stirred for 2–3 hours. To the reaction mixture was added heptane (400 mL) and stirred for 2–3 hours. About 400 mL of solvent mixture was distilled under reduced pressure and heptane (400 mL) was added. The reaction mixture was stirred for 4–6 hours. The reaction mixture was filtered and the damp product was washed with 150 mL heptane and ethanol mixture (4:1) to afford crude Nefazodone Hydrochloride (i.e. Formula 4 above) (137 g, LOD 37.2%, 85% molar yield on dry basis). Part of the damp product (35.0 g) was recrystallized from isopropanol (520 mL) and acetone (25 mL). The resulting damp product was dried under vacuum to afford pharmaceutically acceptable pure Nefazodone Hydrochloride (i.e. Formula 1 above) (20.7 g, 93% molar yield). The overall molar yield from the intermediate Semicarbazide Dihydrochloride (i.e. Formula 3 above) is 79%.

As many changes can be made to the embodiments without departing from the scope of the invention, it is intended that all material be interpreted as illustrative thereof and not in a limiting sense.

The embodiments of the invention in which an exclusive property or privilege is claimed are as follows:

1. A process for the preparation of Nefazodone Hydrochloride comprising reacting semicarbazide dihydrochloride of Formula 3 with triethylorthopropionate using trirnethysilylchloride and hydrochloric acid to convert the semicarbazide dihydrochloride 3 into Nefazodone hydrochloride.

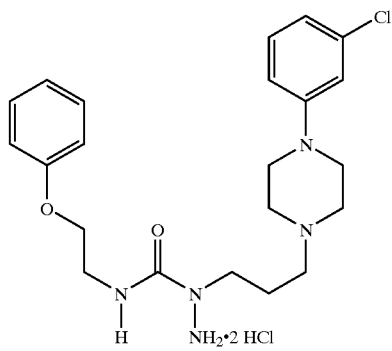

Semicarbazide Dihydrochloride 3.

2. A process for the preparation of Nefazodone Hydrochloride comprising
   (i) adding Semicarbazide of Formula 2 in methanol to hydrochloric acid in isopropanol;

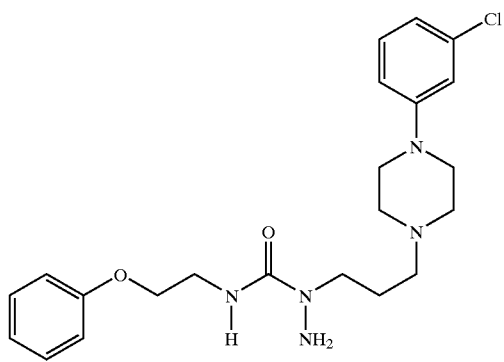

Semicarbazide 2

(ii) heating the mixture to reflux for about 2.5 to about 3.0 hours and subsequently cooling it to room temperature;
   (iii) filtering the reaction mixture and washing the solid with methanol and subsequently drying same under vacuum to afford of Semicarbazide Dihydrochloride of Formula 3;

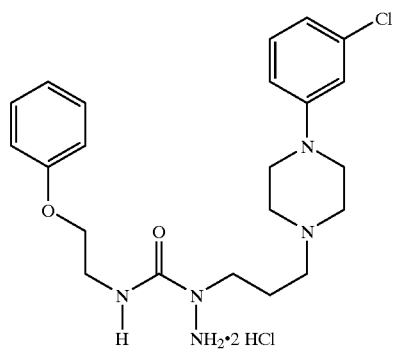

Semicarbazide Dihydrochloride 3

(iv) adding trimethylsilyl chloride slowly to a suspension of Semicarbazide Dihydrochloride in ethanol, followed by triethyl orthopropionate and stirring for 14–16 hours;
   (v) adding hydrochloric acid in isopropanol to the reaction mixture and stirring for 6–8 hours;
   (vi) adding trimethylsilyl chloride to the reaction mixture, followed by triethyl orthopropionate and stirring for 12–14 hours;
   (vii) adding hydrochloric acid in isopropanol to the reaction mixture and stirring for 2–3 hours;
   (viii) adding heptane to the reaction mixture and stirring for 2–3 hours and subsequently distilling of solvent mixture under reduced pressure and adding heptane and stirring for 4–6 hours;
   (ix) filtering the reaction mixture as a damp product and washing same with heptane and ethanol mixture (4:1) to afford crude Nefazodone Hydrochloride.

3. The process of claim 2 wherein the overall molar yield from the intermediate Semicarbazide Dihydrochloride is 79%.

4. The process of claim 2 wherein the damp product was recrystallized from isopropanol and acetone.

5. A process for the preparation of Nefazodone Hydrochloride comprising:
   (i) adding a predetermined amount of semicarbazide of Formula 2 in methanol to a predetermined amount of hydrochloric acid in isopropanol;

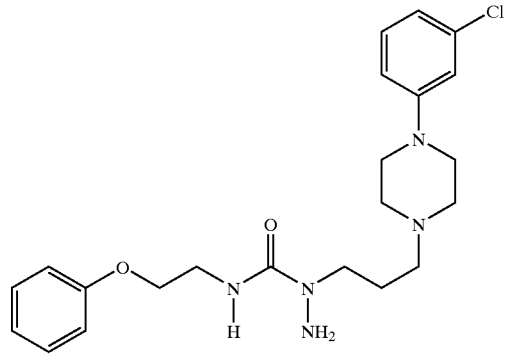

Semicarbazide 2

(ii) heating the mixture to reflux for a predetermined time period and subsequently cooling it to room temperature;

(iii) filtering the reaction mixture and washing the solid with methanol and subsequently drying same under vacuum to afford Semicarbazide Dihydrochloride of Formula 2;

(iv) adding a predetermined amount of trimethylsilyl chloride slowly to a suspension of the Semicarbazide Dihydrochloride in ethanol, followed by a predetermined amount of triethyl orthopropionate and stirring for a predetermined period of time;

(v) adding a predetermined amount of hydrochloric acid in isopropanol to the reaction mixture and stirring for a predetermined amount of time;

(vi) adding a predetermined amount of trimethylsilyl chloride to the reaction mixture, followed by a predetermined amount of triethyl orthopropionate and stirring for a predetermined amount of time;

(vii) adding a predetermined amount of hydrochloric acid in isopropanol to the reaction mixture and stirring for a predetermined amount of time;

(viii) adding a predetermined amount of heptane to the reaction mixture and stirring for a predetermined amount of time and subsequently distilling a predetermined amount of solvent mixture under reduced pressure and adding heptane and stirring for a predetermined amount of;

(ix) filtering the reaction mixture as a damp product and washing same with heptane and ethanol mixture (4:1) to afford crude Nefazodone Hydrochloride.

6. The process of claim 5 wherein the overall molar yield from the intermediate Semicarbazide Dihydrochloride is 79%.

7. The process of claim 5 wherein the damp product was recrystallized from isopropanol and acetone.

8. A process for the preparation of Nefazodone Hydrochloride comprising the following steps:

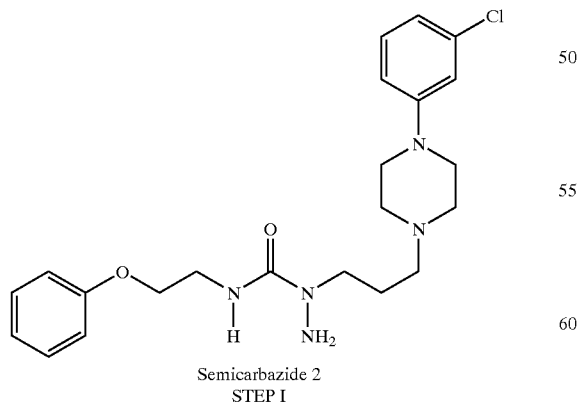

Semicarbazide 2
STEP I

Hydrochloric acid in Alcohol | Methanol (reaction solvent)

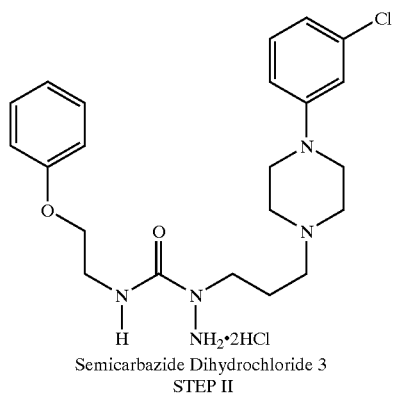

Semicarbazide Dihydrochloride 3
STEP II

Ethanol,
Triethyl orthopropionate,
Trimethylsilyl chloride,
Hydrochloric acid in Alcohol

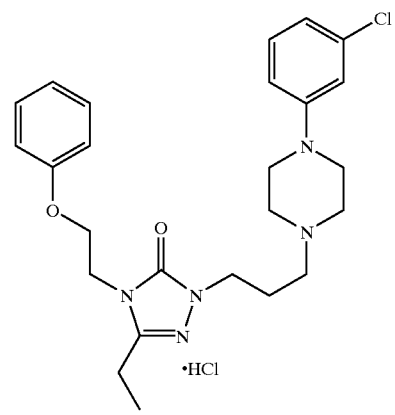

Crude Nefazodone Hydrochloride 4
STEP III

Purification with Alcohol or Alcohol and Acetone or Alcohol and Water

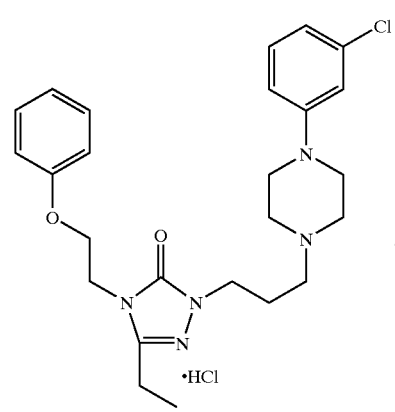

Pure Nefazodone Hydrochloride 1
STEP IV

9. A process for the preparation of Nefazodone Hydrochloride comprising the following steps:

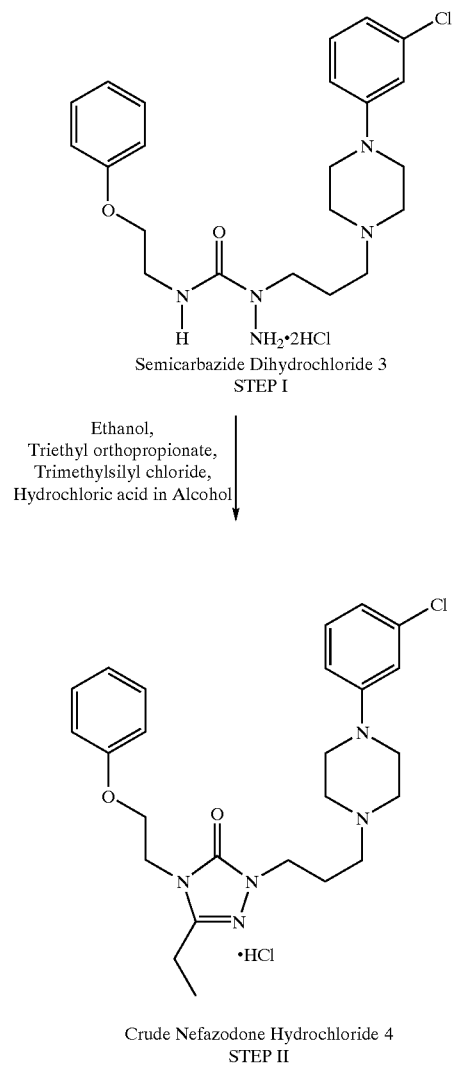

Semicarbazide Dihydrochloride 3
STEP I

Ethanol,
Triethyl orthopropionate,
Trimethylsilyl chloride,
Hydrochloric acid in Alcohol Crude Nefazodone Hydrochloride 4
STEP II 10. The process for the preparation of Nefazodone Hydrochloride of claim 9 further comprising the following step of reacting:

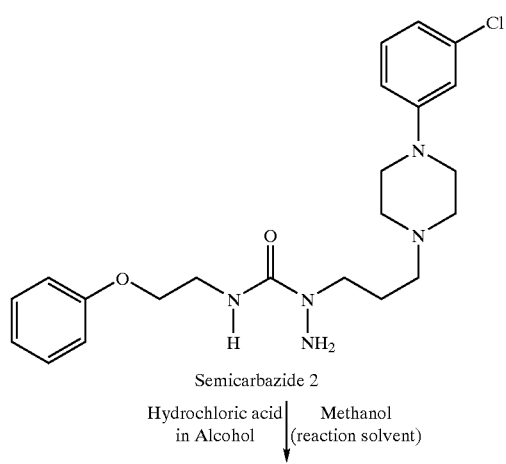

Semicarbazide 2

Hydrochloric acid in Alcohol | Methanol (reaction solvent)

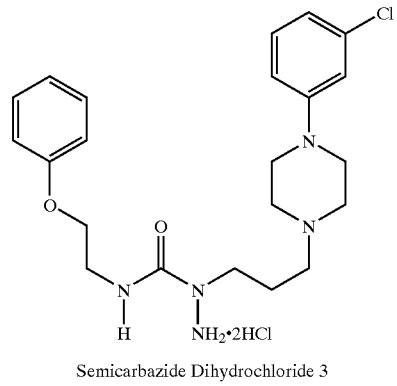

Semicarbazide Dihydrochloride 3

11. The process for the preparation of Nefazodone Hydrochloride of claim 9 or 10 further comprising purifying:

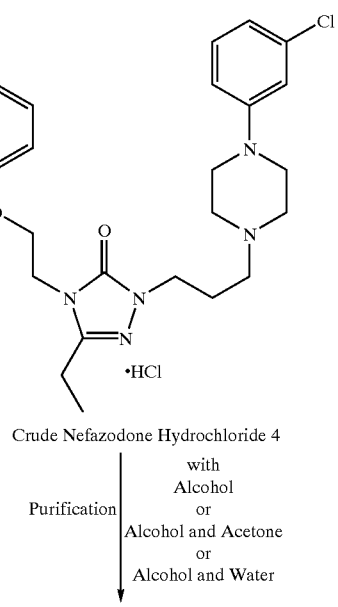

Crude Nefazodone Hydrochloride 4

Purification with Alcohol or Alcohol and Acetone or Alcohol and Water

Pure Nefazodone Hydrochloride 1

12. A process for the preparation of Nefazodone Hydrochloride comprising:

(i) adding a predetermined amount of trimethylsilyl chloride slowly to a suspension of Semicarbazide Dihydrochloride of Formula 3 in ethanol, followed by addition of triethyl orthopropionate;

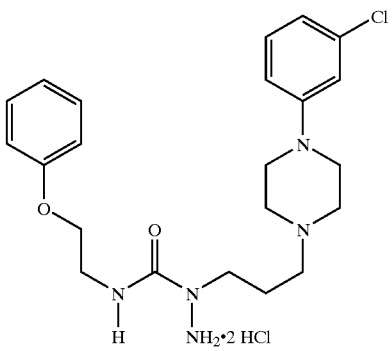

Semicarbazide Dihydrochloride 3

(ii) adding hydrochloric acid in isopropanol to the reaction mixture and mixing;
(iii) adding a predetermined amount of trimethylsilyl chloride to the reaction mixture, followed by triethyl orthopropionate;
(iv) adding hydrochloric acid in isopropanol to the reaction mixture;
(v) adding a predetermined amount of heptane to the reaction mixture and subsequently distilling a predetermined amount of solvent mixture under reduced pressure and adding heptane;
(vi) filtering the reaction mixture as a damp product and washing same with for example heptane and ethanol mixture (4:1) to afford crude Nefazodone Hydrochloride.

13. The process of claim 12 further comprising the following additional steps completed to afford Semicarbazide Dihydrochloride:
(i) adding a predetermined amount of semicarbazide of Formula 2 in methanol to a predetermined amount of hydrochloric acid in isopropanol;

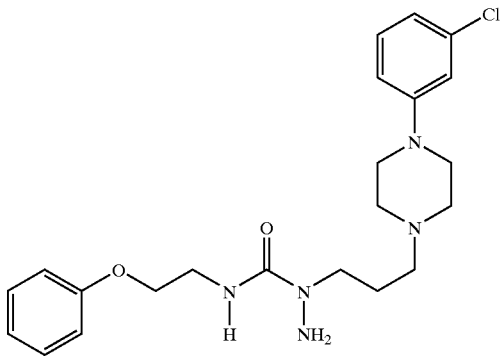

Semicarbazide 2

(ii) heating the mixture to reflux for a predetermined time period and subsequently cooling it to substantially room temperature;
(iii) filtering the reaction mixture and washing the solid with methanol and subsequently drying same under vacuum to afford Semicarbazide Dihydrochloride.

14. The process of claim 12 or 13 further comprising the following step:
drying the resulting damp product of substep (vi) of claim 12 under vacuum to afford pharmaceutically acceptable pure Nefazodone Hydrochloride.

* * * * *